United States Patent
Haeberle et al.

(10) Patent No.: US 9,481,641 B2
(45) Date of Patent: *Nov. 1, 2016

(54) PROCESS FOR THE PURIFICATION OF A POLYCARBODIIMIDE

(71) Applicant: BASF SE, Ludwigshafen (DE)

(72) Inventors: Karl Haeberle, Speyer (DE); Maria Teresa Hechavarria Fonseca, Mannheim (DE); Lars Rehling, Rahden (DE); Frank Schaefer, Stemwede (DE); Fatemeh Ahmadnian, Ludwigshafen (DE); Heinrich Bollmann, Alfhausen (DE); Markus Bubolz, Luebbecke (DE); Carsten Buschmann, Dissen a. T. W. (DE); Guenter Scholz, Lemfoerde (DE); Maria Thomas, Muehlen (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/429,151

(22) PCT Filed: Sep. 19, 2013

(86) PCT No.: PCT/EP2013/069451
§ 371 (c)(1),
(2) Date: Mar. 18, 2015

(87) PCT Pub. No.: WO2014/044742
PCT Pub. Date: Mar. 27, 2014

(65) Prior Publication Data
US 2015/0225336 A1  Aug. 13, 2015

(30) Foreign Application Priority Data

Sep. 19, 2012 (EP) .................................. 12185051

(51) Int. Cl.
| | | |
|---|---|---|
| C07C 267/00 | (2006.01) | |
| C08G 73/00 | (2006.01) | |
| C08G 69/00 | (2006.01) | |
| C08G 18/48 | (2006.01) | |
| C08G 18/65 | (2006.01) | |
| C08G 18/67 | (2006.01) | |
| C08G 18/32 | (2006.01) | |

(52) U.S. Cl.
CPC ......... *C07C 267/00* (2013.01); *C08G 18/3206* (2013.01); *C08G 18/4854* (2013.01); *C08G 18/6511* (2013.01); *C08G 18/6705* (2013.01); *C08G 69/00* (2013.01); *C08G 73/00* (2013.01); *Y02P 20/582* (2015.11)

(58) Field of Classification Search
None
See application file for complete search history.

(56) References Cited

U.S. PATENT DOCUMENTS

| | | |
|---|---|---|
| 5,349,087 A | 9/1994 | West |
| 5,352,400 A | 10/1994 | West |
| 5,354,888 A | 10/1994 | Scholl |
| 5,434,305 A | 7/1995 | Hennig et al. |
| 6,184,410 B1 | 2/2001 | Bollmann et al. |

FOREIGN PATENT DOCUMENTS

| | | |
|---|---|---|
| CN | 1805984 A | 7/2006 |
| CN | 102203211 A | 9/2011 |
| EP | 0 606 698 | 8/1994 |
| JP | 06 298890 | 10/1994 |
| WO | WO 2005/003204 A2 | 1/2005 |
| WO | WO 2010/049467 A1 | 5/2010 |

OTHER PUBLICATIONS

Combined Office Action and Search Report issued Dec. 23, 2015 in Chinese Patent Application No. 201380060184.4 (with English translation of Categories of Cited Documents).
International Search Report Issued Nov. 28, 2013 in PCT/EP13/069451 Filed Sep. 19, 2013.
U.S. Appl. No. 14/767,121, filed Aug. 11, 2015, Adams, et al.

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A process for purifying a polycarbodiimide comprising (a) providing a mixture comprising a polycarbodiimide and a carbodiimidization catalyst; (b) separating carbodiimidization catalyst from the polycarbodiimide by subjecting the mixture according to (a) to a first distillation, (c) adding an entrainer to the first bottom product obtained from (b) to obtain a mixture; (d) further separating carbodiimidization catalyst from the polycarbodiimide by subjecting the mixture obtained from (c) to a second distillation.

17 Claims, 2 Drawing Sheets

PROCESS FOR THE PURIFICATION OF A POLYCARBODIIMIDE

The present invention relates to a process for purifying a polycarbodiimide and further relates to a composition which comprises a polycarbodiimide and has a very low content of a carbodiimidization catalyst.

Polycarbodiimides are well known compounds which, for example, are used as stabilizers to prevent hydrolysis in plastics.

Such polycarbodiimides can be produced by subjecting organic diisocyanates to a decarboxylation and a polymerization reaction. In the simplest way, two diisocyanate molecules are reacted to obtain a carbodiimide.

Further polymerization may lead to oligomers with a plurality of carbodiimide groups and terminal isocyanate groups according to the following formula

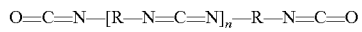

$$O=C=N-[R-N=C=N]_n-R-N=C=O$$

wherein n is typically a number in the range of from 1 to 30.

Usually, this polymerization reaction is performed in the presence of a carbodiimidization catalyst. As carbodiimidization catalyst, an organophosphorus compound can be employed. Such organophosphorus carbodiimidization catalysts are highly active so that the condensation reaction may be performed fast and under mild conditions.

Such highly active catalysts require, however, their complete removal after the polymerization reaction to avoid undesirable side or consecutive reactions. As a consequence of an incomplete catalyst removal, carbodiimides may be obtained which are not storable over long term and further may have adverse effects on the dynamic and static properties of plastics.

Further, organophosphorus carbodiimidization catalysts are expensive compounds. Therefore, their essential complete separation, recovery and repeated use are also desirable from an economical and ecological point of view.

EP-A 0 609 698 discloses a process for the preparation of carbodiimides by polymerizing diisocyanate in the presence of phosphorene oxides. Following the polymerization, the catalyst is removed by distillation at reduced pressure in a stream of $CO_2$ at a temperature in the range of from 100 to 250° C. No residual catalytic activity was determined for the carbodiimides obtained according to the process disclosed in EP-A 0 609 698.

U.S. Pat. No. 6,184,410 B1 discloses carbodiimides obtained by condensation of 1,3-bis(1-methyl-1-isocyanatoethyl)benzene in the presence of organophosphorus catalysts. At the desired polymerization degree, the catalyst and unreacted 1,3-bis(1-methyl-1-isocyanatoethyl)-benzene are distilled off at 180° C. and a pressure of 1 mbar. This document is silent on the amount of residual catalyst in the resulting reaction mixture comprising polycarbodiimide, obtained after distillation.

U.S. Pat. No. 5,434,305 discloses a process for the production of aromatic carbodiimides by carbodiimidization of aromatic monoisocyanates in the presence of catalytically active organic phosphorus compounds. According to U.S. Pat. No. 5,434,305, the unreacted starting isocyanate, i.e. a monoisocyanate, is used as entraining agent for the removal of the catalyst. U.S. Pat. No. 5,434,305 is completely silent on the purification of polycarbodiimides, in particular of polycarbodiimides which are obtained from polymerizing of diisocyanates.

Therefore, it was an object of the present invention to provide a simple and cost-effective process for the purification of polycarbodiimide, particularly an improved process for the removal of the carbodiimidization catalyst from a reaction mixture comprising polycarbodiimide and carbodiimidization catalyst.

It was a further object of the present invention to provide a highly pure polycarbodiimide which, in particular, does not have adverse effects on the static and dynamic properties of plastics such as plastics comprising ester groups.

Therefore, the present invention relates to a process for purifying a polycarbodiimide, comprising:

(a) providing a mixture comprising a polycarbodiimide and a carbodiimidization catalyst;

(b) separating carbodiimidization catalyst from the polycarbodiimide by subjecting the mixture according to (a) to a first distillation, wherein a first bottom product and a first top product are obtained, wherein the first bottom product comprises the polycarbodiimide and carbodiimidization catalyst, wherein the weight ratio of carbodiimidization catalyst relative to polycarbodiimide in the first bottom product is lower than the weight ratio of carbodiimidization catalyst relative to polycarbodiimide in the mixture according to (a), and wherein the first top product comprises carbodiimidization catalyst;

(c) adding an entrainer to the first bottom product obtained from (b) to obtain a mixture, wherein the entrainer has a boiling point which is lower than the boiling point of the polycarbodiimide;

(d) further separating carbodiimidization catalyst from the polycarbodiimide by subjecting the mixture obtained from (c) to a second distillation, wherein a second bottom product and a second top product are obtained, wherein the second bottom product comprises the polycarbodiimide and carbodiimidization catalyst, wherein the weight ratio of carbodiimidization catalyst relative to polycarbodiimide in the second bottom product is lower than the weight ratio of carbodiimidization catalyst relative to polycarbodiimide in the first bottom product obtained from (b), and wherein the second top product comprises carbodiimidization catalyst and entrainer.

Surprisingly, according to the process of the present invention which comprises subjecting a mixture comprising a polycarbodiimide and a carbodiimidization catalyst to two subsequent distillation steps, wherein for the second distillation step an entrainer is used which is added after the first distillation step, the removal of the carbodiimidization catalyst is very effective, and in particular, a highly pure polycarbodiimide is obtained. In particular, the mixture which is obtained as second bottom product from the second distillation step generally comprises polycarbodiimide, carbodiimidization catalyst, and optionally diisocyanate, wherein in this second bottom product preferably at least 99.99% by weight of said composition consist of the polycarbodiimide, the carbodiimidization catalyst and optionally the diisocyanate, and wherein in this second bottom product the weight ratio of the carbodiimidization catalyst relative to the polycarbodiimide is at most 0.2:100,000, preferably at most 0.15 to 100,000, more preferably at most 0.1:100,000.

A further advantage, due to the effective separation, is that the top products of the two distillation steps which contain carbodiimidization catalyst can be used as such as starting material for the production of polycarbodiimide. This is further discussed further hereinbelow. Thus, due to this advantageous recycling of carbodiimidization catalyst, the process of the present invention can be carried out in an essentially product-neutral manner in terms of the catalyst and the diisocyanate.

Still further, the polycarbodiimide obtained by the process of the present invention shows excellent long term storability and is well suited for the use as stabilizer in plastics without having negative effects on their initial stability and processability.

Step (a)

Generally, the mixture according to (a) which comprises polycarbodiimide and carbodiimidization catalyst can be provided in any conceivable manner. Typically, the mixture is obtained by the polymerization of a diisocyanate in the presence of a carbodiimidization catalyst, the resulting mixture comprising polycarbodiimide and carbodiimidization catalyst.

Preferably, the polycarbodiimide comprised in the mixture according to (a) has a degree of polymerization in the range of from 1 to 20, preferably from 2 to 15, more preferably from 2 to 10, more preferably from 3 to 12. The degree of the polymerization of the polycarbodiimide can be controlled by continuously tracing the degree of polymerization of the polycarbodiimide during the polymerization reaction by measuring the amount of free NCO groups by a suitable titration method.

Preferably, the polycarbodiimide comprised in the mixture according to (a) has an NCO content in the range of from 0 to 25% by weight, preferably from 1 to 18% by weight, more preferably from 2 to 15% by weight, more preferably from 3 to 14% by weight, more preferably 4 to 12% by weight, based on the total weight of the polycarbodiimide.

By way of example, and in case 1,3-bis(2-isocyanato-2-propyl)benzene (TMXDI) is used as diisocyanate starting material for the production of polycarbodiimide for providing the mixture in (a), a polymerization degree of 12.8 of the obtained polycarbodiimide corresponds to an NCO content of the polycarbodiimide of about 3% by weight.

Preferably, the carbodiimidization catalyst comprised in the mixture according to (a) comprises at least an organophosphorous compound selected from the group consisting of phospholenes, phospholene oxides, phospholines, phospholine oxides and mixtures of two or more thereof. In addition to the at least one organophosphorous compound, the carbodiimidization catalyst may contain at least one further component which may either catalytically active or essentially inert under polymerization conditions. More preferably, the carbodiimidization catalyst comprised in the mixture according to (a) comprises, preferably consists of an organophosphorous compound selected from the group consisting of phospholene oxides and mixtures of two or more phospholene oxides. More preferably, the carbodiimidization catalyst comprised in the mixture according to (a) comprises, preferably consists of a phospholene oxide.

In particular, the carbodiimidization catalyst comprises, preferably consists of, a phospholene oxide of the general formula (1) and double bond isomers thereof,

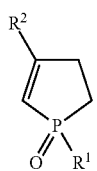

(1)

wherein $R^1$ and $R^2$ are independently H or a suitably substituted or unsubstituted aliphatic $C_1$-$C_{15}$ hydrocarbon residue, cycloaliphatic $C_5$-$C_{15}$ hydrocarbon residue, aryl $C_6$-$C_{15}$ hydrocarbon residue, aralkyl $C_6$-$C_{15}$ hydrocarbon residue, or alkaryl $C_6$-$C_{15}$ hydrocarbon residue, more preferably H or a $C_1$-$C_{10}$ hydrocarbon residue.

Preferably, $R^1$ is H or a substituted or unsubstituted aliphatic $C_1$-$C_{10}$ hydrocarbon residue, or aryl $C_6$-$C_{15}$ hydrocarbon residue. More preferably, $R^1$ is a substituted or unsubstitued methyl, ethyl or propyl or a substituted or unsubstituted phenyl or benzyl. More preferably, $R^1$ is methyl or phenyl.

Preferably, $R^2$ is H or a substituted or unsubstituted aliphatic $C_1$-$C_{10}$ hydrocarbon residue. More preferably, $R^2$ is H or a substituted or unsubstituted methyl, ethyl or propyl. More preferably, $R^2$ is H or methyl.

Examples of the phospholene oxides include 3-methyl-1-phenyl-2-phospholene-1-oxide, 1-phenyl-2-phospholene-1-oxide, 1-methyl-2-phospholene-1-oxide, 1,3-dimethyl-2-phospholene-1-oxide, 1-ethyl-3-methyl-2-phospholene-1-oxide and double bond isomers thereof.

Further suitable carbodiimidization catalysts may comprise, preferably consist of, an organophosphorus compound selected from the group consisting of diphenylphosphinic acid and salts thereof, bis-(2,4,-trimethylpentyl)-phosphinic acid, tributylphosphane, triisobutylphosphane sulfide, trialkylphosphane oxides such as trioctylphosphane oxide or trihexylphosphane oxide, triphenylphosphane, tetraphenylphosphine bromide, tetrabutylphosphine chloride, tetrabutylphosphine bromide, bis(2,4,4-trimethylpentyl)-ditiophosphonic acid, bis(2,4,4-trimethylpentyl)-monothiophosphonic acid, and mixtures of two or more thereof.

Preferably, the carbodiimidization catalyst comprised in the mixture according to (a) comprises, preferably consists of, 1-methyl-2-phospholene-1-oxide (MPO).

Generally, it may be conceivable to employ two or more different carbodiimidization catalysts for preparing the mixture according to (a), and therefore, it may be conceivable that the mixture according to (a) comprises two or more different carbodiimidization catalysts. In this case, it would be preferred that at least one of these carbodiimidization catalysts, more preferably all of these carbodiimidization catalysts are selected from the preferred carbodiimidization catalysts mentioned above. Most preferably, only one carbodiimidization catalyst is employed for preparing the mixture according to (a), and therefore, it is most preferred that the mixture according to (a) comprises exactly one carbodiimidization catalyst.

In a preferred embodiment, the weight ratio of carbodiimidization catalyst relative to polycarbodiimide in the mixture according to (a) is in the range of from 0.02:100 to 2:100, preferably from 0.02:100 to 1:100, more preferably from 0.02:100 to 0.5:100, more preferably from 0.02:100 to 0.25:100.

Typically, the mixture according to (a) further comprises a diisocyanate. This diisocyanate additionally comprised in the mixture according to (a) may be residual diisocyanate which has not been reacted to give the polycarbodiimide, in case the mixture according to (a) is the result of the polymerization of diisocyanate in the presence of carbodiimidization catalyst. As described in detail hereinunder, this diisocyanate is at least partially separated in step (b) from the polycarbodiimide. Depending on the preparation process of the polycarbodiimide and the respective starting materials, it may conceivable that the mixture according to (a) comprises two or more different diisocyanates. In this case, it would be preferred that at least one, preferably all of these diisocyanates are at least partially separated from polycarbodiimide in step (b).

Preferably, the diisocyanate comprised in the mixture according to (a) and at least partially separated in (b) has the formula R(NCO)$_2$, wherein R is selected from the group consisting of linear or branched aliphatic $C_3$-$C_{15}$ hydrocarbon residues, cycloaliphatic $C_5$-$C_{20}$ hydrocarbon residues, aryl $C_6$-$C_{18}$ hydrocarbon residues, alkaryl $C_6$-$C_{20}$ hydrocarbon residues, and aralkyl $C_6$-$C_{20}$ hydrocarbon residues. As mentioned above, it is conceivable that two or more of these diisocyanates may be comprised in the mixture according to (a).

More preferably, the diisocyanate comprised in the mixture according to (a) is selected from the group consisting of methylene diisocyanate, dimethylene diisocyanate, trimethylene diisocyanate, tetramethylene diisocyanate, pentamethylene diisocyanate, dipropylether diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, 1,4-butylene glycol dipropylether diisocyanate, thiodihexyl diisocyanate, metaxylylene diisocyanate, paraxylylene diisocyanate, 4,4'-dicyclohexylmethane diisocyanate (HMDI), 1,3-bis(2-isocyanato-2-propyl)benzene (TMXDI), toluene diisocyanate (TDI) and diphenylmethane diisocyanate (MDI), isophorone diisocyanate (IPDI), hexamethylene diisocyanate (HDI) and 1,12-diisocyanatedodecane (DDI). As mentioned above, it is conceivable that two or more of these diisocyanates may be comprised in the mixture according to (a).

Even more preferably, the diisocyanate comprised in the mixture according to (a) is selected from the group consisting of tetramethylene diisocyanate, hexamethylene diisocyanate (HDI), dodecamethylene diisocyanate, 1,4-diisocyanatocyclohexane, trimethylhexane diisocyanate, 2,2-bis(4-isocyanatocyclohexyl)-propane, isophorone diisocyanate (IPDI), 4,4'-dicyclohexylmethane diisocyanate (HMDI), 1,3-bis(2-isocyanato-2-propyl)benzene (TMXDI), toluene diisocyanate (TDI) and diphenylmethane diisocyanate (MDI), the diisocyanate preferably being 1,3-bis(2-isocyanato-2-propyl)benzene (TMXDI). As mentioned above, it is conceivable that two or more of these diisocyanates may be comprised in the mixture according to (a).

In a particularly preferred embodiment, the diisocyanate comprised in the mixture according to (a) is 1,3-bis(2-isocyanato-2-propyl)benzene (TMXDI).

The amount of diisocyanate comprised in the mixture according to (a) is not particularly restricted and typically may depend on the polymerization conditions in case the mixture according to (a) is provided by a method comprising polymerizing a diisocyanate in the presence of the carbodiimidization catalyst.

Generally, the weight ratio of diisocyanate relative to polycarbodiimide in the mixture according to (a) may be in the range of from 0:100 to 1,000:100. Preferably, the weight ratio of diisocyanate relative to polycarbodiimide in the mixture according to (a) is in the range of from 1:100 to 1,000:100, more preferably from 1:100 to 500:100, more preferably from 1:100 to 100:100.

According to a preferred embodiment of the present invention, the mixture according to (a) is provided by a method comprising polymerizing a diisocyanate, preferably a preferred diisocyanate as defined above, most preferably 1,3-bis(2-isocyanato-2-propyl)benzene (TMXDI), in the presence of a carbodiimidization catalyst, preferably in the presence of a preferred carbodiimidization catalyst as defined above, most preferably 1-methyl-2-phospholene-1-oxide (MPO), at a temperature in the range of from 20 to 300° C. and a pressure in the range of 10 to 1,000 mbar, preferably in the range of 10 to 800 mbar.

More preferably, the mixture according to (a) is provided by said method which comprises polymerizing the diisocyanate in the presence of the carbodiimidization catalyst in a reaction vessel in liquid phase at a temperature in the range of from 20 to 250° C., preferably from 130 to 200° C., at a pressure in the range of 10 to 2000 mbar, preferably from 20 to 800 mbar, preferably from 200 to 500 mbar, and in the presence of at least one inert gas, preferably selected from the group consisting of nitrogen, helium, neon, argon, carbon dioxide, and a mixture of two or more thereof, most preferably nitrogen, wherein the at least one inert gas is introduced into the liquid phase in the reaction vessel with a flow rate in the range of from 0.1 x/h to 100 x/h, x being the volume of the reaction vessel. Even more preferably, the polymerization according to said method is carried out in the absence of a solvent. Therefore, according to a preferred embodiment of the present invention, the mixture according to (a) does not contain a solvent.

Preferably, at least 80% by weight, more preferably at least 90% by weight, more preferably at least 95% by weight, more preferably at least 99 by weight of the mixture according to (a) consist of polycarbodiimide, carbodiimidization catalyst, and optionally diisocyanate. Within above-defined limits, the mixture according to (a) may comprise further components which may also be removed at least partially in (b), for example as one or more separate fractions. Further components may be for example by-products and/or side-products obtained after polymerization of diisocyanate in the presence of carbodiimidization catalyst.

Step (b)

According to step (b) of the process of the present invention, carbodiimidization catalyst is separated from the polycarbodiimide by subjecting the mixture according to (a) to a first distillation, wherein a first bottom product and a first top product are obtained, wherein the first bottom product comprises the polycarbodiimide and carbodiimidization catalyst, wherein the weight ratio of carbodiimidization catalyst relative to polycarbodiimide in the first bottom product is lower than the weight ratio of carbodiimidization catalyst relative to polycarbodiimide in the mixture according to (a), and wherein the first top product comprises carbodiimidization catalyst. Since according to the invention, the boiling point of the carbodiimidization catalyst is lower than the boiling point of the polycarbodiimide, the carbodiimidization catalyst will be predominantly contained in the first top product during (b) whereas, under suitable conditions, the polycarbodiimide will be predominantly contained in the first bottom product.

Thus, the mixture according to (a) may be prepared either in the distillation apparatus used for the separation in step (b) or prepared in a given vessel or reactor and then transferred in said distillation apparatus.

The distillation apparatus which is used in step (b) is not subjected to any particular restrictions. Typically, the distillation apparatus may be equipped with heating means and/or stirring means and/or vacuum means, condensing means, feeding and removal means and the like. The distillation apparatus may be made of materials which are inert under distillation conditions. By way of example, glass or stainless steel may be mentioned.

According to the present invention, the distillation may be performed as batch process, semi-continuous process, or as continuous process.

In the batch distillation, the distillation apparatus is charged with a given amount of the mixture according to (a). Under distillation conditions, the mixture according to (a) is then separated in the first bottom product and the first top product. Alternatively, as mentioned above, the mixture according to (a) is prepared in the distillation apparatus, and, after polymerization, the polymerization conditions such as temperature, pressure, stirring rate, flow of inter gas, or the like, are switched off, and the distillation conditions are established. For example, the mixture according to (a) can be prepared in a suitable reaction vessel, and after polymerization, said vessel is equipped with suitable condensing and removal means and the distillation according to (b) is started.

Preferably, the removal of carbodiimidization catalyst from the mixture according to (a) is performed in (b) until a rise in the distillation temperature is observed. Additionally or alternatively, the amount of carbodiimidization catalyst in the first bottom product may be determined by a suitable analysis technique.

According to an embodiment of the present invention, the first bottom product can be removed from the distillation apparatus and suitably stored. The distillation apparatus is then charged with fresh mixture according to (a), and the distillation according to (b) is carried out to obtain a second batch of the first bottom product. This method can be repeated until to complete amount of mixture (a) has been subjected to distillation according to (b). The batches of the first bottom product can be suitably combined and be subjected to stages (c) and (d) of the present invention. According to a preferred embodiment of the present invention, the first bottom product remains in the distillation apparatus after distillation according to (b), and is subjected to stages (c) and (d) of the present invention.

In a continuous distillation, the mixture according to (a) comprising polycarbodiimide and carbodiimidization catalyst is fed without interruption into the distillation apparatus and the separated fractions are removed continuously as output streams in (b). Consequently, a first bottom product and a first top product are removed continuously as two independent output streams of the distillation apparatus.

Further according to the present invention, the distillation according to (b) may be performed as standard distillation or as fractional distillation. According to standard distillation, the carbodiimidization catalyst vapor produced during heating is immediately liquefied in a condenser. Preferably, standard distillation is employed in case the boiling point of the carbodiimidization catalyst is at least about 25° C. lower than the boiling point of the polycarbodiimide. According to fractional distillation, the mixture according to (a) comprising polycarbodiimide and a carbodiimidization catalyst is subjected to repeated vaporization-condensation cycles with a fractionating column. This separation technique which is also referred to as rectification, may be employed in case the boiling point of the carbodiimidization catalyst is less than 25° C. lower than the boiling point of the polycarbodiimide. A fractionating column may be provided inside with horizontal plates or trays or the column may be packed with a packing material. There are no particular restrictions regarding the type of packing material. The packing material may be Raschig rings or structured sheet metal. Further, reflux may be used to achieve a more efficient separation.

Preferably, the distillation in (b) is performed at a reduced pressure of less than 1 bar. Preferably, the pressure under which the distillation in (b) is performed is in the range of from 0.01 to 950 mbar, more preferably from 0.05 to 900 mbar. Preferably, the pressure under which the distillation in (b) is performed is in the range of from 0.1 to 800 mbar, more preferably from 0.1 to 500 mbar, more preferably from 0.1 to 300 mbar such as from 0.1 to 200 mbar or from 0.2 to 100 mbar or from 0.1 to 10 mbar. Preferably, the distillation in (b) is performed at a temperature in the range of from 100 to 400° C., more preferably from 130 to 350° C., more preferably from 150 to 250° C. such as from 150 to 200° C. or from 175 to 225° C. or from 200 to 250° C.

After the first distillation according to (b), the weight ratio of carbodiimidization catalyst relative to polycarbodiimide in the first bottom product is reduced relative to the weight ratio of carbodiimidization catalyst relative to polycarbodiimide in the mixture according to (a). Preferably, the weight ratio of carbodiimidization catalyst relative to polycarbodiimide in the first bottom product obtained from (b) is at most 2:100,000, more preferably at most 1:100,000, more preferably at most 0.5:100,000, more preferably at most 0.2:100,000, more preferably in the range of from 0.2:100,000 to 2:100,000, more preferably from 0.2:100,000 to 1:100,000, more preferably from 0.2:100,000 to 0.5:100,000.

When diisocyanate is additionally comprised in the mixture according to (a), at least a part of the diisocyanate is separated in (b) from the polycarbodiimide, so that the first top product obtained from (b) comprises carbodiimidization catalyst and further comprises diisocyanate. It is further preferred that in (b) the diisocyanate is separated essentially completely from the polycarbodiimide. Thus, at least 50% by weight, more preferably at least 70% by weight, more preferably at least 80% by weight of the diisocyanate comprised in the mixture according to (a) are separated from the polycarbodiimide in step (b). Preferably, the weight ratio of diisocyanate relative to polycarbodiimide in the first bottom product obtained from (b) is in the range of from 0.1:100 to 20:100, preferably from 0.1:100 to 10:100, more preferably from 0.1:100 to 1:100.

Preferably, the first top product obtained from (b) essentially consists of carbodiimidization catalyst and optionally diisocyanate. Preferably, at least 90% by weight, more preferably at least 95% by weight, more preferably at least 99% by weight, more preferably at least 99.9% by weight, more preferably at least 99.99% by weight of the first top product consist of carbodiimidization catalyst and optionally diisocyanate.

The first top product comprising carbodiimidization catalyst and optionally diisocyanate may be reused as starting material for the production of polycarbodiimide. Thus, this top product can be recycled as starting material and passed to step (a) of the process of the present invention in case the mixture according to (a) is provided by preparing according to a method as, for example, defined above. If necessary, it is easy to adjust the weight ratio of carbodiimidization catalyst relative to diisocyanate to the limits indicated above prior to the reuse by adding fresh diisocyanate or carbodiimidization catalyst.

Step (c)

According to the process of the present invention, an entrainer which has a boiling point which is lower than the boiling point of the polycarbodiimide is added in step (c) to the first bottom product obtained in (b) to obtain a mixture.

As mentioned above, according to a preferred embodiment of the present invention, the entrainer is added to the first bottom product after distillation in (b) wherein the first bottom product remains in the distillation apparatus. According to one embodiment, after the first distillation, the first bottom product can be cooled to a given temperature, the entrainer is added to the first bottom product and the resulting mixture is then subjected to the distillation conditions as described hereinunder. It is also possible to keep the first bottom product at the temperature under which distillation in (b) was carried out and add the entrainer to obtain the mixture. According to this embodiment, the entrainer, prior to adding to the first bottom product, can be heated, preferably to a temperature in the range of the temperature under which the distillation in (b) was carried out. The energy for heating the entrainer can be at least partially provided, for example, via heat exchange with the first top product and/or the second top product in a suitable heat exchanger. Generally, the entrainer can be continuously added to the mixture obtained from (b) prior to and during distillation according to (d). According to a preferred embodiment, the total amount of entrainer is added to the mixture obtained from (b) to obtain a mixture which is then subjected to distillation.

Generally, the amount of entrainer added in (c) can be adjusted to the specific needs of the separation task according to step (d) of the present invention. Preferably, the entrainer is added in (c) in an amount so that in the resulting mixture, the weight ratio of polycarbodiimide relative to added entrainer is in the range of from 10:100 to 1,000:100, preferably in the range of 20:100 to 500:100, more preferably in the range of 40:100 to 250:100, more preferably in the range of 100:100 to 250:100.

Preferably, the entrainer which is added in (c) as separation aid and which has boiling point lower than the boiling point of the polycarbodiimide has a boiling point in the range of from 150 to 350° C. at ambient pressure, more preferably from 180 to 320° C., more preferably from 200 to 300° C.

To avoid undesirable interaction of the entrainer with the polycarbodiimide and further the diisocyanate, it is especially preferred that the entrainer does not comprise an aminic —NH— group or an —OH group or an —SH group or a —COOH group. More preferably, the entrainer does not comprise an aminic —NH— group and an —OH group, or an aminic —NH— group and an —SH group, or an aminic —NH— group and a —COOH group, or an —OH group and an —SH group, or an —OH group and a —COOH group, or an —SH group and a —COOH group. More preferably, the entrainer does not comprise an aminic —NH— group and an —OH group and an —SH group, or an aminic-NH— group and an —SH group and a —COOH group, or an —OH group and an —SH group and a —COOH group. More preferably, the entrainer does not comprise an aminic —NH— group and an —OH group and an —SH group and a —COOH group. Therefore, the present invention also relates to above-defined process according wherein the entrainer added in (c) does not comprise an aminic-NH— group and/or an —OH group and/or an —SH group and/or a —COOH group.

Preferably, the entrainer is selected from the group consisting of substituted or unsubstituted, linear or branched aliphatic $C_1$-$C_{20}$ hydrocarbons, cycloaliphatic $C_5$-$C_{20}$ hydrocarbons, aryl $C_6$-$C_{18}$ hydrocarbons, alkaryl $C_6$-$C_{20}$ hydrocarbons, or aralkyl $C_6$-$C_{20}$ hydrocarbons. The entrainer may comprise one or more ether, ester, keto, amide, or isocyanate groups. Further, the entrainer may be substituted with one or more halogen residues. Preferably, the entrainer comprises at least one isocyanate group.

Preferably, the entrainer added in (c) is a diisocyanate. More preferably, the entrainer added in (c) is a diisocyanate and is identical with the diisocyanate optionally comprised in the mixture according to (a).

More preferably, the entrainer added in (c) has the formula $R(NCO)_2$, wherein R is selected from the group consisting of linear or branched aliphatic $C_3$-$C_{15}$ hydrocarbon residues, cycloaliphatic $C_5$-$C_{20}$ hydrocarbon residues, aryl $C_6$-$C_{18}$ hydrocarbon residues, alkaryl $C_6$-$C_{20}$ hydrocarbon residues, and aralkyl $C_6$-$C_{20}$ hydrocarbon residues.

Specific diisocyanates which may be used a entrainer according to the process of the present invention are diisocyanates selected from the group consisting of methylene diisocyanate, dimethylene diisocyanate, trimethylene diisocyanate, tetramethylene diisocyanate, pentamethylene diisocyanate, dipropylether diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, 1,4-butylene glycol dipropylether diisocyanate, thiodihexyl diisocyanate, metaxylylene diisocyanate, paraxylylene diisocyanate, 4,4'-dicyclohexylmethane diisocyanate (HMDI), 1,3-bis(2-isocyanato-2-propyl)benzene (TMXDI), toluene diisocyanate (TDI), diphenlymethane diisocyanate (MDI), isophorone diisocyanate (IPDI), hexamethylene diisocyanate (HDI) and 1,12-diisocyanatedodecane (DDI).

More preferably the entrainer added in (c) is selected from the group consisting of tetramethylene diisocyanate, hexamethylene diisocyanate (HDI), dodecamethylene diisocyanate, 1,4-diisocyanatocyclohexane, trimethylhexane diisocyanate, 2,2-bis(4-isocyanatocyclohexyl)-propane, isophorone diisocyanate (IPDI), 4,4'-dicyclohexylmethane diisocyanate (HMDI), 1,3-bis(2-isocyanato-2-propyl)benzene (TMXDI), toluene diisocyanate (TDI) and diphenylmethane diisocyanate (MDI), the diisocyanate preferably being 1,3-bis(2-isocyanato-2-propyl)benzene (TMXDI).

In a particularly preferred embodiment, the entrainer added in (c) is 1,3-bis(2-isocyanato-2-propyl)benzene (TMXDI).

Step (d)

According to step (d) of the present invention, a second distillation step is performed in (d) to further lower the carbodiimidization catalyst content of the polycarbodiimide. From this distillation, a second bottom product and a second top product are obtained, wherein the second bottom product comprises the polycarbodiimide and carbodiimidization catalyst, wherein the weight ratio of carbodiimidization catalyst relative to polycarbodiimide in the second bottom product is lower than the weight ratio of carbodiimidization catalyst relative to polycarbodiimide in the first bottom product obtained from (b), and wherein the second top product comprises carbodiimidization catalyst and entrainer.

In a preferred embodiment, the second distillation is performed in the same distillation apparatus used in (b). Thus, the first bottom product is not removed from the bottom of the distillation apparatus used in (b).

Generally, it is also conceivable that the second distillation is performed in a distillation apparatus which is different from the distillation apparatus used in (b). Accordingly, the first bottom product obtained in (b) could be transferred to a second distillation apparatus which is used for the second distillation according to (d). The addition of the entrainer to the first bottom product to obtain a mixture according to (c) could take place prior to, during, or after the transfer of the first bottom product into the second distillation apparatus.

The distillation apparatus which is used in step (d), if it is different from the distillation apparatus used in in (b), is not subjected to any particular restrictions. Typically, the distillation apparatus may be equipped with heating means and/or stirring means and/or vacuum means, condensing means, feeding and removal means and the like. The distillation apparatus is made of materials which are inert under distillation conditions. By way of example, glass or stainless steel may be mentioned. According to the present invention, the distillation in (d) may be performed as batch process, semi-continuous process, or as continuous process, and further, is can may be performed in batch mode or in continuous mode and may further be performed as standard distillation or as fractionated distillation.

Preferably, the distillation in (d) is performed at a reduced pressure of less than 1 bar. Preferably, the pressure under which the distillation in (d) is performed is in the range of from 0.01 to 950 mbar, more preferably from 0.05 to 900 mbar. Preferably, the pressure under which the distillation in (d) is performed is in the range of from 0.1 to 800 mbar, more preferably from 0.1 to 500 mbar, more preferably from 0.1 to 300 mbar such as from 0.1 to 200 mbar or from 0.2 to 100 mbar or from 0.1 to 10 mbar. Preferably, the distillation in (d) is performed at a temperature in the range of from 100 to 400° C., preferably from 130 to 350° C., more preferably from 150 to 250° C. such as from 150 to 200° C. or from 175 to 225° C. or from 200 to 250° C.

After the second distillation according to (d), the weight ratio of carbodiimidization catalyst relative to polycarbodiimide in the second bottom product is reduced relative to the weight ratio of carbodiimidization catalyst relative to polycarbodiimide in the first bottom product. Preferably, the weight ratio of carbodiimidization catalyst relative to polycarbodiimide in the second bottom product obtained from (d) is at most 0.2:100,000, more preferably at most 0.15:100,000, more preferably at most 0.1:100,000, more preferably in the range of from 0.001:100,000 to 0.2:100,000, more preferably from 0.001:100,000 to 0.15:100,000, more preferably from 0.001:100,000 to 0.1:100,000.

In the second bottom product, diisocyanate may be present. In this case, the weight ratio of the diisocyanate relative to the polycarbodiimide in the second bottom product is preferably at most 10:100, more preferably at most 5:100, more preferably at most 2:100, more preferably at most 1:100, more preferably at most 0.5:100.

Preferably, the second bottom product obtained from (d) essentially consists of polycarbodiimide and optionally of diisocyanate. More preferably, at least 90% by weight, more preferably at least 95% by weight, more preferably at least 99% by weight, more preferably at least 99.9% by weight, more preferably at least 99.99% by weight of the second bottom product consist of polycarbodiimide, carbodiimidization catalyst and optionally diisocyanate.

Therefore, the present invention also relates to a composition containing a polycarbodiimide and a carbodiimidization catalyst and optionally a diisocyanate, wherein at least 99.99% by weight of the composition consist of the polycarbodiimide, the carbodiimidization catalyst and optionally the diisocyanate, and wherein the weight ratio of the carbodiimidization catalyst relative to the polycarbodiimide is at most 0.2:100,000, preferably at most 0.15:100,000, more preferably at most 0.1:100,000, and wherein the weight ratio of the diisocyanate relative to the polycarbodiimide is at most 10:100, preferably at most 5:100, more preferably at most 2:100. Preferably, said composition is obtainable or obtained by the process as defined hereinabove.

Preferably, the inventive composition containing a polycarbodiimide and a carbodiimidization catalyst and optionally a diisocyanate has an advantageous color index, preferably of at most 20, more preferably of at most 25, more preferably of at most 10, more preferably of at most 5, as determined according to DIN 6162, wherein the polycarbodiimide comprised in the mixture has an NCO content in the range of from 0 to 25% by weight, preferably from 1 to 18% by weight, more preferably from 2 to 15% by weight, based on the total weight of the polycarbodiimide.

Preferably, the second top product obtained from (d) essentially consists of carbodiimidization catalyst and entrainer, preferably the diisocyanate. More preferably, at least 99% by weight, more preferably at least 99.9% by weight, more preferably at least 99.99% by weight of the second top product consist of carbodiimidization catalyst and entrainer, preferably diisocyanate. Preferably, in the second top product obtained from (d), the weight ratio of carbodiimidization catalyst, relative to entrainer, preferably diisocyanate, is in the range of from 1 wppm to 10,000 wppm, preferably from 1 wppm to 1,000 wppm, more preferably from 1 wppm to 100 wppm.

The second top product comprising carbodiimidization catalyst and diisocyanate may be reused as starting material for the production of polycarbodiimide. Thus, this top product can be recycled as starting material and passed to step (a) of the process of the present invention in case the mixture according to (a) is provided by preparing according to a method as, for example, defined above. If necessary, it is easy to adjust the weight ratio of carbodiimidization catalyst relative to diisocyanate to the limits indicated above prior to the reuse by adding fresh diisocyanate or carbodiimidization catalyst.

Thus, according to a preferred embodiment of the present invention according to which the entrainer employed in (c) is the diisocyanate used for the preferred preparation of the polycarbodiimide in (a), which diisocyanate is optionally contained in the mixture according to (a), the top products from both distillations in (b) and (d) can be recycled as starting materials into the method for preparation the polycarbodiimide according to (a). Compared to the methods of the prior art, where an inert gas such as carbon dioxide is used as entrainer, the present invention provides a process with essentially no loss of material such as offgas from distillation or the like. Therefore, due to the inventive material-neutral process design, a highly advantageous process is provided. It is thus particularly preferred that the first top product obtained from (b) comprising carbodiimidization catalyst and/or the second top product obtained from (d) comprising carbodiimidization catalyst is/are at least partially, preferably completely recycled as starting material for polymerizing the diisocyanate in the presence of the carbodiimidization catalyst.

Therefore, the present invention also relates to the use of a diisocyanate as entrainer for separating carbodiimidization catalyst from polycarbodiimide, preferably wherein the polycarbodiimide had been prepared from the diisocyanate in the presence of the carbodiimidization catalyst.

The polycarbodiimide obtainable or obtained by the process of the present invention and/or the inventive composition containing a polycarbodiimide and a carbodiimidization catalyst and optionally a diisocyanate may be further employed, such as stabilizers or cross-linking agents.

If used as a stabilizer, it is preferred to increase the solubility and homogeneous distribution of the polycarbodiimides. Having a good compatibility with ester type resins, the polycarbodiimide may be easily added during the synthesis of the resin or during the processing of the resin. Depending of the nature of the resin, the polycarbodiimides may be covalently modified with hydrophilic or hydrophobic compounds. The hydrophilic or hydrophobic compounds react preferably via terminal NCO groups with the polycarbodiimide of the present invention.

The polycarbodiimide of the present invention may be preferably modified with a compound selected from the group consisting of monools, diols, polyoxyalkylene alcohols, monoamines, polyethylene glycols and polypropylene glycols.

It is also conceivable that the diisocyanate may be partly modified with these compounds first, followed by a polymerization of the modified diisocyanate in the presence of a carbodiimidization catalyst.

Suitable monools are selected from the groups consisting of methanol, ethanol, n-propanol, isopropanol, n-butanol, sec-butanol, n-pentanol, technical pentanol mixtures, n-hexanol, technical hexanol mixtures, 2-ethylhexanol, octanol, 2-ethyloctanol, decanol, dodecanol, cyclohexanol and benzyl alcohol, and mixtures of two or more thereof.

Suitable diols are selected from the group consisting of 1,2-ethanediol, 1,3-propanediol, 1,2-propanediol, 1,4-butanediol, 2,4-butanediol, 2,3-butanediol, 1,5-pentanediol, 1,6-hexanediol, 1,7-heptanediol, 1,8-octanediol, 1,10-decanediol, neopentylglycol, 2-methylpropanedi-1,3-ol, 2-ethylpentanedi-1,5-ol, 3-methylpentanedi-1,5-ol, and mixtures of two or more thereof.

Suitable polyoxyalkylene alcohols are preferably alkoxypolyoxyalkylene alcohols selected from the group consisting of polyoxybutylene alcohol, polyoxypropylene alcohol, polyoxypropylenepolyoxyethylene alcohol, polyoxyethylene alcohol and mixtures of two or more thereof, and which may contain a bonded methoxy, ethoxy, n- or isopropoxy or n-butoxy group as terminal alkoxy group.

Suitable monoamines are selected from the group consisting of methylamine, ethylamine, propylamine, butylamine, pentylamine, hexylamine, 1-ethylhexylamine, octylamine, decylamine, diethylamine, dipropylamine, dibutylamine, methylbutylamine, ethylbutylamine, ethylhexyamine, and mixtures of two or more thereof.

Suitable polyethylene glycols have a number average molecular weight (Mn) in the range of from 200 to 6,000 g/mol, more preferable of 400 to 5,000 g/mol, more preferably of from 400 to 3000 g/mol, more preferably of from 400 to 2,000 g/mol. Suitable polypropylene glycols have a number average molecular weight (Mn) in the range of from 200 to 6,000 g/mol, more preferable of 400 to 5,000 g/mol, more preferably of from 400 to 3000 g/mol, more preferably of from 400 to 1,000 g/mol.

The polycarbodiimides of the present invention are particularly useful as stabilizers for ester comprising polymers such as thermoplastic polyesters such as polyethyleneterephthalates, polybutylentherephthalates, polyetheresters, polyesteramides, polycaprolactones and unsaturated polyesterresins and polyesteresters, such as blockcopolymers of polyethyleneterephthalates or polybutyleneterephthalates, or for polymers comprising polyamides.

In cases where the polycarbodiimide is used as a cross-linking agent for a resin, the polycarbodiimide is favorably modified with a compound comprising at least one double bond, preferably at least one olefinic double bond. Preferably, a compound comprising at least one double bond and a functional group capable of reacting with terminal NCO groups is used to further modify the polycarbodiimide.

Specific compounds comprising at least one double bond and a functional group capable of reacting with terminal NCO groups are selected from the group consisting of 2-hydroxyethyl acrylate, 2-hydroxyethyl methacrylate, 2-hydroxypropyl acrylate, 2-hydroxypropyl methacrylate, pentaerythritol triacrylate, pentaerythritol trimethyacrylate, allyl alcohol, 3-butene-1-ol, 4-pentene-1-ol, allylamine, N-methylallylamine, N-ethyl-2-methylallylamine, diallylamine, allylcyclohexylamine, 2-allylphenol, 2-allyloxyethanol, pentaerythritol triallyl ether, polyethylene glycol monomethacrylate, polypropylene glycol monomethacrylate, polyethylene glycol monoacrylate, 2-hydroxy-1,3-dimethacryloxypropane, polypropylene glycol monoacrylate and the like.

Thus, the polycarbodiimides of the present invention may be favorably used as cross linkers in water soluble polymers. The polycarbodiimide obtained by the process of the present invention may be added to a resin having a group capable of reacting with polycarbodiimide, for example, an acrylic resin or natural rubber or synthetic rubber supplied in a form of emulsion (latex) to cross-link the resin and confer further stability to the resin.

It is understood that the polycarbodiimides of the present invention modified with a compound with cross-linking ability may be act as hydrolysis stabilizers as well. Advantageously, by forming a covalent bond with the resin, bleeding out of the resin is prevented, thereby enhancing the stabilizing performance and keeping the required amounts of polycarbodiimide low. It is understood that high amounts of polycarbodiimides function as plasticizer and the original performance of the resin is thereby deteriorated.

The concentration of the polycarbodiimides of the invention in the polymers to be stabilized or cross-linked is in the range of from 0.05 to 10% by weight, preferably in the range of 0.1 to 5% by weight.

The present invention is further characterized by the following specific embodiments and the combinations of embodiments resulting from the respective back-references and combinations of back-references:

1. A process for purifying a polycarbodiimide, comprising:
   (a) providing a mixture comprising a polycarbodiimide and a carbodiimidization catalyst;
   (b) separating carbodiimidization catalyst from the polycarbodiimide by subjecting the mixture according to (a) to a first distillation, wherein a first bottom product and a first top product are obtained, wherein the first bottom product comprises the polycarbodiimide and carbodiimidization catalyst, wherein the weight ratio of carbodiimidization catalyst relative to polycarbodiimide in the first bottom product is lower than the weight ratio of carbodiimidization catalyst relative to polycarbodiimide in the mixture according to (a), and wherein the first top product comprises carbodiimidization catalyst;
   (c) adding an entrainer to the first bottom product obtained from (b) to obtain a mixture, wherein the entrainer has a boiling point which is lower than the boiling point of the polycarbodiimide;
   (d) further separating carbodiimidization catalyst from the polycarbodiimide by subjecting the mixture obtained from (c) to a second distillation, wherein a second bottom product and a second top product are obtained, wherein the second bottom product comprises the polycarbodiimide and carbodiimidization catalyst, wherein the weight ratio of carbodiimidization catalyst relative to polycarbodiimide in the second bottom product is lower than the weight ratio of carbodiimidization catalyst relative to polycarbodiimide in the first bottom product obtained from (b), and wherein the second top product comprises carbodiimidization catalyst and entrainer.

2. The process according to embodiment 1, wherein the weight ratio of carbodiimidization catalyst relative to polycarbodiimide in the mixture according to (a) is in the range of from 0.02:100 to 2:100, preferably from 0.02:100 to 1:100, more preferably from 0.02:100 to 0.5:100, more preferably from 0.02:100 to 0.25:100.

3. The process according to embodiment 1 or 2, wherein the weight ratio of carbodiimidization catalyst relative to polycarbodiimide in the bottom product obtained from (b) is at most 2:100,000, preferably at most 1:100,000, preferably at most 0.5:100,000, preferably at most 0.2:100,000, preferably in the range of from 0.2:100,00 to 2:100,00, preferably from 0.2:1000,000 to 1:100,00, preferably from 0.2:100,000 to 0.5:100,000.

4. The process according to any of embodiments 1 to 3, wherein the weight ratio of carbodiimidization catalyst relative to polycarbodiimide in the bottom product obtained from (d) is at most 0.2:100,000, preferably at most 0.15:100,000, more preferably at most 0.1:100,000.

5. The process according to any of embodiments 1 to 4, wherein the entrainer added in (c) has a boiling point in the range of from 150 to 350° C. at ambient pressure.

6. The process according to any of embodiments 1 to 5, wherein the entrainer added in (c) does not comprise an aminic —NH— group and/or an —OH group and/or an —SH group and/or a —COOH group.

7. The process according to any of embodiments 1 to 6, wherein the entrainer added in (c) is a diisocyanate.

8. The process according to any of embodiments 1 to 7, wherein the entrainer added in (c) has the formula $R(NCO)_2$, wherein R is selected from the group consisting of linear or branched aliphatic $C_3$-$C_{15}$ hydrocarbon residues, cycloaliphatic $C_5$-$C_{20}$ hydrocarbon residues, aryl $C_6$-$C_{18}$ hydrocarbon residues, alkaryl $C_6$-$C_{20}$ hydrocarbon residues, and aralkyl $C_6$-$C_{20}$ hydrocarbon residues.

9. The process according to any of embodiments 1 to 8, wherein the entrainer added in (c) is 1,3-bis(2-isocyanato-2-propyl)benzene (TMXDI).

10. The process according to any of embodiments 1 to 9, wherein the mixture according to (a) further comprises a diisocyanate, wherein in (b) the diisocyanate is at least partially separated from the polycarbodiimide and the first top product obtained from (b) further comprises diisocyanate.

11. The process according to embodiment 10, wherein the diisocyanate has the formula $R(NCO)_2$, wherein R is selected from the group consisting of linear or branched aliphatic $C_3$-$C_{15}$ hydrocarbon residues, cycloaliphatic $C_5$-$C_{20}$ hydrocarbon residues, aryl $C_6$-$C_{18}$ hydrocarbon residues, alkaryl $C_6$-$C_{20}$ hydrocarbon residues, and aralkyl $C_6$-$C_{20}$ hydrocarbon residues.

12. The process according to embodiment 10 or 11, wherein the diisocyanate is selected from the group consisting of tetramethylene diisocyanate, hexamethylene diisocyanate (HDI), dodecamethylene diisocyanate, 1,4-diisocyanato-cyclohexane, trimethylhexane diisocyanate, 2,2-bis(4-isocyanatocyclohexyl)-propane, isophorone diisocyanate (IPDI), 4,4'-dicyclohexylmethane diisocyanate (HMDI), 1,3-bis(2-isocyanato-2-propyl)benzene (TMXDI), toluene diisocyanate (TDI) and diphenlymethane diisocyanate (MDI), the diisocyanate preferably being 1,3-bis(2-isocyanato-2-propyl)benzene (TMXDI).

13. The process according to any of embodiments 10 to 12, wherein the weight ratio of diisocyanate relative to polycarbodiimide in the mixture according to (a) is in the range of from 1:100 to 1000:100 preferably from 1:100 to 500:100, more preferably from 1:100 to 100:100.

14. The process according to any of embodiments 10 to 13, wherein the entrainer added in (c) is the diisocyanate further comprised in the mixture according to (a).

15. The process according to any of embodiments 10 to 14, wherein in (c) the weight ratio of polycarbodiimide relative to added entrainer is in the range of from 10:100 to 1000:100, preferably in the range of 20:100 to 500:100, more preferably in the range of 40:100 to 250:100, more preferably in the range of 100:100 to 250:100.

16. The process according to any of embodiments 1 to 15, wherein the distillation in (b) is performed at a temperature in the range of from 100 to 400° C., preferably from 130 to 350° C., more preferably from 150 to 250° C.

17. The process according to any of embodiments 1 to 16, wherein the distillation in (d) is performed at a temperature in the range of from 100 to 400° C., preferably from 130 to 350° C., more preferably from 150 to 250° C.

18. The process according to any of embodiments 1 to 17, wherein the distillation in (b) is performed at a pressure in the range of from 0.1 to 800 mbar, preferably from 0.1 to 500 mbar, more preferably from 0.1 to 300 mbar.

19. The process according to any of embodiments 1 to 18, wherein the distillation in (d) is performed at a pressure in the range of from 0.1 to 800 mbar, preferably from 0.1 to 500 mbar, more preferably from 0.1 to 300 mbar.

20. The process according to any of embodiments 1 to 19, wherein the carbodiimidization catalyst comprises, preferably consists of, an organophosphorous compound selected from the group consisting of phospholenes, phospholene oxides, phospholidines, phospholine oxides and mixtures of two or more thereof.

21. The process according to any of embodiments 1 to 20, wherein the carbodiimidization catalyst comprises, preferably consists of, 1-methyl-2-phospholene-1-oxide.

22. The process according to any of embodiments 1 to 21, wherein the polycarbodiimide comprised in the mixture according to (a) has a degree of polymerization in the range of from 1 to 20, preferably from 2 to 15.

23. The process according to any of embodiments 1 to 22, wherein the polycarbodiimide comprised in the mixture according to (a) has an NCO content in the range of from 0 to 25% by weight, preferably from 1 to 18% by weight, more preferably from 2 to 15% by weight, based on the total weight of the polycarbodiimide.

24. The process according to any of embodiments 1 to 23, wherein the mixture according to (a) comprising a polycarbodiimide and a carbodiimidization catalyst is provided by a method comprising polymerizing a diisocyanate, preferably a diisocyanate as defined in claim 11 or 12, in the presence of the carbodiimidization catalyst at a temperature in the range of from 20 to 300° C. and a pressure in the range of 10 to 1,000 mbar.

25. The process according to embodiment 24, wherein the method comprises polymerizing the diisocyanate in the presence of the carbodiimidization catalyst in a reaction vessel in liquid phase at a temperature in the range of from 20 to 250° C., at a pressure in the range of from 20 to 800 mbar and in the presence of at least one inert gas, wherein the at least one inert gas is introduced into the liquid phase in the reaction vessel with a flow rate in the range of from 0.1 x/h to 100 x/h, x being the volume of the reaction vessel.

26. The process according to embodiment 24 or 25, wherein the first top product obtained from (b) comprising carbodiimidization catalyst and/or the second top product obtained from (d) comprising carbodiimidization catalyst is/are at least partially, preferably completely recycled as starting material for polymerizing the diisocyanate in the presence of the carbodiimidization catalyst to obtain the mixture according to (a).

27. A composition containing a polycarbodiimide, a carbodiimidization catalyst, and optionally a diisocyanate.

wherein at least 99.99% by weight of said composition consists of the polycarbodiimide and the optional diisocyanate and wherein the weight ratio in said composition of the carbodiimidization catalyst relative to the polycarbodiimide is at most 0.2:100,000, preferably at most 0.15:100,000, preferably at most 0.1:100,000.

28. The composition of embodiment 27, obtainable or obtained by a process according to any of embodiments 1 to 26.

29. The composition of embodiment 27 or 28, having a color index of at most 20, preferably of at most 10, more preferably of at most 5, as determined according to DIN 6162, wherein the polycarbodiimide comprised in the mixture has an NCO content in the range of from 0 to 25% by weight, preferably from 1 to 18% by weight, more preferably from 2 to 15%, based on the total weight of the polycarbodiimide.

30. Use of a diisocyanate as entrainer for separating carbodiimidization catalyst from polycarbodiimide, preferably wherein the polycarbodiimide had been prepared from the diisocyanate in the presence of the carbodiimidization.

31. An integrated process for the preparation and purification of a polycarbodiimide, said process comprising
   (a) preparing a mixture comprising a polycarbodiimide, a carbodiimidization catalyst and optionally a diisocyanate by polymerizing the polycarbodiimide from the diisocanate in the presence of the carbodiimidization catalyst;
   (b) separating carbodiimidization catalyst from the polycarbodiimide by subjecting the mixture according to (a) to a first distillation, wherein a first bottom product and a first top product are obtained, wherein the first bottom product comprises the polycarbodiimide and carbodiimidization catalyst, wherein the weight ratio of carbodiimidization catalyst relative to polycarbodiimide in the first bottom product is lower than the weight ratio of carbodiimidization catalyst relative to polycarbodiimide in the mixture according to (a), and wherein the first top product comprises carbodiimidization catalyst and optionally diisocyanate;
   (c) adding an entrainer to the first bottom product obtained from (b) to obtain a mixture, wherein the entrainer has a boiling point which is lower than the boiling point of the polycarbodiimide, wherein the entrainer is the diisocyanate from which the polycarbodiimide is polymerized in (a);
   (d) further separating carbodiimidization catalyst from the polycarbodiimide by subjecting the mixture obtained from (c) to a second distillation, wherein a second bottom product and a second top product are obtained, wherein the second bottom product comprises the polycarbodiimide and carbodiimidization catalyst, wherein the weight ratio of carbodiimidization catalyst relative to polycarbodiimide in the second bottom product is lower than the weight ratio of carbodiimidization catalyst relative to polycarbodiimide in the first bottom product obtained from (b), and wherein the second top product comprises carbodiimidization catalyst and entrainer;
   (e) at least partially, preferably completely recycling the first top product obtained from (b) and/or the second top product obtained from (d) into (a) as starting material for polymerizing the diisocyanate in the presence of the carbodiimidization catalyst.

32. The integrated process of embodiment 31, wherein in (c), the entrainer added to the first bottom product obtained from (b) is the diisocyanate from which the polycarbodiimide is polymerized in (a).

33. The integrated process of embodiment 31 or 32, wherein in (a), the mixture is prepared by polymerizing the diisocyanate in the presence of the carbodiimidization catalyst in a reaction vessel in liquid phase at a temperature in the range of from 20 to 250° C., preferably from 130 to 200° C., at a pressure in the range of from 10 to 2000 mbar, preferably from 20 to 800 mbar, preferably from 200 to 500 mbar, and in the presence of at least one inert gas, preferably selected from the group consisting of nitrogen, helium, neon, argon, carbon dioxide, and a mixture of two or more thereof, most preferably nitrogen, wherein the at least one inert gas is introduced into the liquid phase in the reaction vessel with a flow rate in the range of from 0.1 x/h to 100 x/h, x being the volume of the reaction vessel. Even more preferably, the polymerizetion according to said method is carried out in the absence of a solvent. Therefore, according to a preferred embodiment of the present invention, the mixture according to (a) does not contain a solvent.

The present invention is illustrated by the following examples, comparative examples, and figures.

EXAMPLES

Preparation of Polycarbodiimide

Example 1

410 parts per weight TMXDI with an NCO content of 34.4% by weight and 0.82 parts per weight MPO were charged in a 1000 ml four neck flask. The mixture was stirred and heated in the absence of a solvent at a temperature of 180° C. and a pressure of 300 mbar. When a NCO content of 12.8% by weight was determined for the reaction mixture, the catalyst and residual TMXDI were removed in batch mode by standard distillation using a Liebig condenser at a temperature of 190° C. and a pressure of 0.2 mbar. The NCO content of the bottom product in % by weight was determined by standard titration following DIN EN 1242. The first distillation yielded as bottom product 280 parts per weight polycarbodiimide with an NCO content of 7.7% by weight and further containing 10 wppm MPO. The MPO content of the bottom product was determined by chromatography.

After the first distillation, 100 parts per weight TMXDI were added to the polycarbodiimide in the four neck flask and the mixture was subjected at a second standard distillation using a Liebig condenser in batch mode at a temperature of 190° C. and a pressure of 0.2 mbar to further remove catalyst and to remove the added TMXDI.

After the second distillation, 280 parts per weight polycarbodiimide with a NCO content of 7.7% by weight and containing <1 wppm MPO were obtained as bottom product.

Example 2 (Comparative Example)

Example 2 was carried out as described in Example 1, except that no TMXDI was added and no second distillation was performed.

After the first distillation, 280 parts per weight polycarbodiimide with an NCO content of 7.7% by weight and containing 5 wppm MPO were obtained.

Example 3 (Comparative Example)

Example 3 was carried out as described in Example 1, except that also no TMXDI was added and no second distillation was performed.

After the first distillation, 280 parts per weight polycarbodiimide with an NCO content of 7.7% by weight and containing 10 wppm MPO were obtained.

Use of the Polycarbodiimide as Stabilizer

Example 4

An MDI prepolymer, which is commonly used as a polymer precursor in the synthesis of polyurethanes, was stored for 24 hours at 130° C. in the presence of polycarbodiimide obtained according to Example 1. The MDI prepolymer consisted of 87% by weight 4,4'-diphenylmethane diisocyanate (MDI), 8.1% by weight dipropylene glycol and 4.9% by weight polypropylene glycol with an OH number of 93.5 mg KOH/g. The weight ratio of MDI prepolymer relative to the polycarbodiimide was 9:1.

Only a very low amount of foaming was observed for the mixture which further changed its color to yellow. However, no change of viscosity was observed (see FIG. 1, left bottle). The color was further measured according to DIN EN 1557 and had expressed in Hazen units a value of 800.

Therefore, by the process of the present invention as performed in Example 1, a highly pure polycarbodiimide containing less than 1 wppm MPO was obtained. Thus, the process of the present invention yields a polycarbodiimide comprising significantly less MPO relative to a purification process according as performed in Comparative Examples 2 and 3 yielding a polycarbodiimide with a MPO content of 5 and 10 ppm, respectively.

Example 5 (Comparative Example)

Example 5 was performed as described in Example 4, except that polycarbodiimide obtained in Example 2 was used. Foaming was observed and the mixture turned solid and yellow (see FIG. 1, middle bottle). The color value in Hazen units was also 800.

Example 6 (Comparative Example)

Example 6 was performed as described in Example 4, except that polycarbodiimide obtained in Example 3 was used. For the mixture, a very strong foaming and also solidification was observed. In addition, the mixture adapted a dark yellow color (see FIG. 1, right bottle). The color value in Hazen units was determined to be >1000.

Example 7

A mixture comprising pure and colorless MDI, which is commonly used as a starting material in the synthesis of polyurethanes, and polycarbodiimide obtained in Example 1 in a weight ratio of 9:1 was stored for 24 hours at 80° C. The sample maintained its initial low viscosity and no foaming and yellowing could be observed (FIG. 2, left bottle). The color value determined in Hazen units was 300.

Example 8 (Comparative Example)

Example 8 was performed as described in Example 7, except that polycarbodiimide obtained in Example 2 was used. For the sample an increase of viscosity and a yellow color could be observed (FIG. 2, middle bottle). The color value expressed in Hazen units was 600.

Example 9 (Comparative Example)

Example 9 was performed as described in Example 7, except that polycarbodiimide obtained in Example 3 were used. Again, for the sample foaming, a high viscosity and a yellow color could be observed (FIG. 2, right bottle). The color value expressed in Hazen units was 700.

The results of Examples 4 to 9 are summarized in Table 1:

TABLE 1

Results of Examples 4 to 9

| Example No. | Substrate | Stabilizer | Storage | Visual effects | Viscosity | Color | Color in Hazen units (DIN EN 1557) |
|---|---|---|---|---|---|---|---|
| 4 | MDI prepolymer | polycarbodiimide with <1 wppm MPO | 24 h/130° C. | light foaming | viscous | yellow | 800 |
| 5 (Comp. Ex.) | MDI prepolymer | polycarbodiimide with 5 wppm MPO | 24 h/130° C. | foaming | solid | yellow | 800 |
| 6 (Comp. Ex.) | MDI prepolymer | polycarbodiimide with 10 wppm MPO | 24 h/130° C. | strong foaming | solid | dark yellow | >1000 |
| 7 | MDI | polycarbodiimide with <1 wppm MPO | 24 h/80° C. | none | low viscosity | colorless | 300 |
| 8 (Comp. Ex.) | MDI | polycarbodiimide with 5 wppm MPO | 24 h/80° C. | none | viscous | yellow | 600 |
| 9 (Comp. Ex.) | MDI | polycarbodiimide with 10 wppm MPO | 24 h/80° C. | foaming | highly viscous | yellow | 700 |

In Example 4, the MDI prepolymer was stored in the presence of polycarbodiimide obtained according to the process of the present invention comprising less than 1 wppm carbodiimidization catalyst. The mixture according to Example 4 had a yellow color and a very low amount of foaming was observed.

In contrast, in Comparative Examples 5 and 6 polycarbodiimides were used as stabilizers comprising 5 wppm and 10 wppm carbodiimidization catalysts, respectively. After the storage for 24 hours at high temperatures, foaming and a yellow color were observed for the mixture of Comparative Example 5. Further, for the mixture of Comparative Example 6 a very strong foaming and a deep yellow color (Hazen number >1000) were observed when compared with Example 4. In addition, the mixtures according to Comparative Examples 5 and 6 turned solid when compared with Example 4.

This indicates that considerable amount of undesired reactions have taken place between the MDI prepolymer and the residual carbodiimidization catalyst present in the polycarbodiimide in Comparative Examples 5 and 6.

These results show that the polycarbodiimide of the invention has excellent stabilizing properties without significantly impairing the dynamic properties of prepolymers and consequently of polymers. This is a remarkable result since in the MDI prepolymer a high number of reactive NCO groups are present which may for example easily polymerize to polycarbodiimides in the presence of carbodiimidization catalyst. Such a polymerization is an undesirable side reaction, for example in the synthesis of polyurethanes.

Example 7 and Comparative Examples 8 and 9 have been performed similarly to Examples 4 to 6, except that pure MDI was used instead of MDI prepolymer. The mixture of Example 7 comprising MDI and the polycarbodiimide obtained according to the process of the present invention had a low viscosity and was still colorless after storage for 24 hours at 80° C. (Hazen number of 300).

For the mixture of Comparative Example 8 comprising MDI and further polycarbodiimide, the polycarbodiimide comprising 5 wppm carbodiimidization catalyst, an increase in viscosity and yellowing was observed after storage when compared with Example 7. Further, for the mixture of Comparative Example 9 comprising MDI and further polycarbodiimide, which comprised 10 wppm carbodiimidization catalyst, foaming as well as a strong viscosity increase and yellowing was observed after storage when compared with Example 7.

In Example 7, the polycarbodiimide obtained according to the present invention does not alter significantly the dynamic properties and visual appearance of a polymer starting material and consequently of a polymer resin itself in an unfavorable manner. The polycarbodiimide obtained according to the present invention are therefore well suited as stabilizers in polymer resins.

In contrast, the results obtained in Comparative Examples 8 and 9 indicate that undesired reactions occurred between MDI which has two free NCO groups per molecule, and that the residual carbodiimidization catalyst present in the polycarbodiimide has negative effects on dynamic properties and visual appearance.

Example 10

A thermoplastic polyurethane (TPU) obtained via standard methods from 29 parts per weight MDI, 7.7 parts per weight 1,4-butanediol and 63 parts per weight of a polyethylene glycol adipate ester with an OH number of 50.6 mg KOH/g and 0.3 parts per weight polycarbodiimide according to Example 1 were heated at 80° C. for 15 hours.

The obtained polyester TPU was formed via injection molding at 200° C. into test plates with the dimensions of 110×100×2 mm. From these plates samples were cut corresponding to DIN 53504. The samples were submitted to further extensive testing.

Example 11 (Comparative Example)

Polyester TPU moldings were produced as described in Example 10, except that 0.3 parts per weight polycarbodiimide obtained in Example 2 were used. The moldings were subjected to the same tests as the moldings of Example 10.

The results of the testing of Example 10 and Comparative Example 11 are summarized in Table 2.

TABLE 2

Results of the testing of Example 10 and Comparative Example 11

| Test | Standard | Unit | Results Ex. 10 | Results Comp. Ex. 11 |
|---|---|---|---|---|
| Density | DIN EN ISO 1183-1A | g/cm$^3$ | 1.246 | 1.247 |
| Hardness (Shore A) | DIN 53505 | | 86 | 85 |
| Tensile strength | DIN 53504 | MPa | 50 | 45 |
| Elongation | | % | 670 | 670 |
| Tear resistance | DIN ISO 34-1, B (b) | kN/m | 94 | 94 |
| Abrasion | DIN 53516 | mm$^3$ | 42 | 56 |
| Yellowness-Index | ASTM 313 | | 13 | 8 |
| Tensile strength after hydrolysis | Hydrolysis performed in water at 80° C. for 21 d (Ex. 11) and for 14 d (Comp. Ex. 12), DIN EN ISO 527 | MPa/ (% loss) | 41 (−18%) | 32 (−29%) |
| Appearance | | | opaque | opaque |

The moldings obtained according to Example 10 had a favorable tensile strength which was about 10% higher than the tensile strength of the moldings obtained according to Comparative Example 11. Further, the abrasion value of the moldings according to Example 10 was favorably decreased by about 30% compared with the abrasion values of the moldings according to Comparative Example 11.

The tensile strength was also measured after the moldings of Example 10 and Comparative Example 11 had been submitted to hydrolysis. The moldings of Example 10 were stored in water at 80° C. for 21 days. The moldings of Comparative Example 11 were stored in water at 80° C. for 14 days. Although the moldings of Comparative Example 11 were stored only for 14 days in water already a loss of tensile strength of 29% was observed. This is in contrast to the moldings of Example 10, which were obtained using the polycarbodiimide obtained by the process of the present invention, where only a loss of 18% was obtained after 21 days of hydrolysis.

These favorable results indicate that the process of the present invention yields a polycarbodiimide which yields a significantly better long term storability and stability of plastics.

CITED LITERATURE

Figure 1:
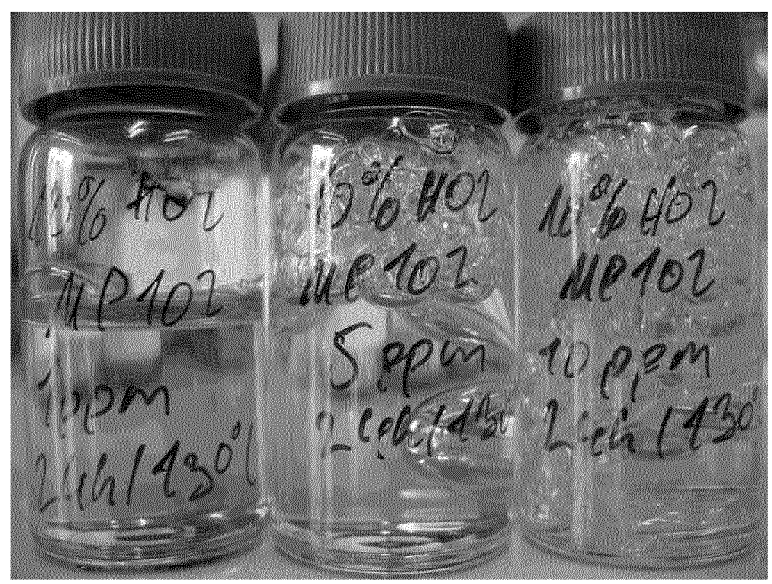
FIG. 1 shows a mixture comprising MDI prepolymer, which consists of 4,4'-diphenylmethane diisocyanate (MDI), dipropylene glycol and polypropylene glycol, and comprising polycarbodiimide in a weight ratio of 9:1 after storage for 24 hours at 130° C., the polycarbodiimide comprising 1 wppm MPO (left bottle, Example 4), 5 wppm MPO (middle bottle, Example 5 (comparative example)) and 10 wppm (right bottle, Example 6 (comparative example)). The mixture in the left bottle is yellow and shows very little foaming. The mixture in the middle bottle has a yellow color and shows foaming. The mixture in the right bottle shows strong foaming and has a deep yellow color.
Figure 2:
FIG. 2 shows a mixture comprising MDI and polycarbodiimide in a weight ratio of 9:1 after storage for 24 hours at 130° C., the polycarbodiimide comprising 1 wppm MPO (left bottle, Example 7), 5 wppm MPO (middle bottle, Example 8 (comparative example)) and 10 wppm (right bottle, Example 10 (comparative example)). The mixture in the left bottle is colorless and shows no foaming. The mixture in the middle bottle is yellow and shows no foaming. The mixture in the right bottle is yellow and shows foaming.

EP-A 0 609 698
U.S. Pat. No. 6,184,410
U.S. Pat. No. 5,434,305

The invention claimed is:

1. A process for purifying a polycarbodiimide, comprising:
   (a) separating a carbodiimidization catalyst from an initial mixture comprising a polycarbodiimide and the carbodiimidization catalyst by subjecting the initial mixture to a first distillation, wherein a first bottom product and a first top product are obtained, wherein the first bottom product comprises the polycarbodiimide and carbodiimidization catalyst, a weight ratio of carbodiimidization catalyst relative to polycarbodiimide in the first bottom product is lower than a weight ratio of carbodiimidization catalyst relative to polycarbodiimide in the initial mixture and wherein the first top product comprises carbodiimidization catalyst;
   (b) adding an entrainer to the first bottom product obtained from (a) to obtain an intermediate mixture, wherein the entrainer has a boiling point which is lower than the boiling point of the polycarbodiimide;
   (c) further separating carbodiimidization catalyst from the polycarbodiimide by subjecting the intermediate mixture obtained from the adding (b) to a second distillation, wherein a second bottom product and a second top product are obtained, wherein the second bottom product comprises the polycarbodiimide and carbodiimidization catalyst, a weight ratio of carbodiimidization catalyst relative to polycarbodiimide in the second bottom product is lower than a weight ratio of carbodiimidization catalyst relative to polycarbodiimide in the first bottom product obtained from the separating (a), and wherein the second top product comprises carbodiimidization catalyst and entrainer.

2. The process according to claim 1, wherein the weight ratio of carbodiimidization catalyst relative to polycarbodiimide in the initial mixture is from 0.02:100 to 2:100.

3. The process according to claim 1, wherein the weight ratio of carbodiimidization catalyst relative to polycarbodiimide in the bottom product obtained from the separating (a) is at most 2:100,000.

4. The process according to claim 1, wherein the weight ratio of carbodiimidization catalyst relative to polycarbodiimide in the bottom product obtained from the further separating (c) is at most 0.2:100,000.

5. The process according to claim 1, wherein the entrainer added in the adding (b) has a boiling point in the range of from 150 to 350° C. at ambient pressure.

6. The process according to claim 1, wherein the entrainer added in (b) does not comprise an aminic —NH— group, an —OH group, an —SH group and/or a —COOH group.

7. The process according to claim 1, wherein the entrainer added in (b) is a diisocyanate.

8. The process according to claim 1, wherein the entrainer added in (b) has the formula $R(NCO)_2$, wherein R is selected from the group consisting of linear or branched aliphatic $C_3$-$C_{15}$ hydrocarbon residues, cycloaliphatic $C_5$-$C_{20}$ hydrocarbon residues, aryl $C_6$-$C_{18}$ hydrocarbon residues, alkaryl $C_6$-$C_{20}$ hydrocarbon residues, and aralkyl $C_6$-$C_{20}$ hydrocarbon residues.

9. The process according to claim 1, wherein the entrainer added in (b) is 1,3-bis(2-isocyanato-2-propyl)benzene (TMXDI).

10. The process according to claim 1, wherein the initial mixture further comprises a diisocyanate, wherein in the separating (a) the diisocyanate is at least partially separated from the polycarbodiimide and the first top product obtained from the separating (a) further comprises diisocyanate.

11. The process according to claim 10, wherein the diisocyanate has the formula $R(NCO)_2$, wherein R is selected from the group consisting of linear or branched aliphatic $C_3$-$C_{15}$ hydrocarbon residues, cycloaliphatic $C_5$-$C_{20}$ hydrocarbon residues, aryl $C_6$-$C_{18}$ hydrocarbon residues, alkaryl $C_6$-$C_{20}$ hydrocarbon residues, and aralkyl $C_6$-$C_{20}$ hydrocarbon residues.

12. The process according to claim 10, wherein the diisocyanate is selected from the group consisting of tetramethylene diisocyanate, hexamethylene diisocyanate (HDI), dodecamethylene diisocyanate, 1,4-diisocyanatocyclohexane, trimethylhexane diisocyanate, 2,2-bis(4-isocyanatocyclohexyl)-propane, isophorone diisocyanate (IPDI), 4,4'-dicyclohexylmethane diisocyanate (HMDI), 1,3-bis(2-isocyanato-2-propyl)benzene (TMXDI), toluene diisocyanate (TDI) and diphenylmethane diisocyanate (MDI).

13. The process according to claim 10, wherein the entrainer added in (b) is the diisocyanate further comprised in the initial mixture.

14. The process according to claim 10, wherein in adding (b) the weight ratio of polycarbodiimide relative to added entrainer is in the range of from 10:100 to 1,000:100.

15. The process according to claim 1, wherein the carbodiimidization catalyst comprises at least one organophosphorous compound selected from the group consisting of phospholenes, phospholene oxides, pholidines, and phospholine oxides.

16. The process according to claim 1, wherein the initial mixture comprising a polycarbodiimide and a carbodiimidization catalyst is obtained by a method comprising polymerizing a diisocyanate in the presence of the carbodiimidization catalyst at a temperature in the range of from 20 to 300° C. and a pressure in the range of from 10 to 800 mbar.

17. The process according to claim 16, wherein the first top product obtained from the separating (a) comprising carbodiimidization catalyst and/or the second top product obtained from the further separating (c) comprising carbodiimidization catalyst is/are at least partially recycled as starting material for polymerizing the diisocyanate in the presence of the carbodiimidization catalyst to obtain the initial mixture.

* * * * *